United States Patent [19]
Rogers et al.

[11] 3,957,997
[45] May 18, 1976

[54] ANTICOCCIDIAL COMPLEXES OF 4,4'-DINITROCARBANILIDES

[75] Inventors: Edward F. Rogers, Middletown; Richard A. Dybas, Edison; John Hannah, Matawan, all of N.J.

[73] Assignee: Merck & Co., Inc., Rahway, N.J.

[22] Filed: Sept. 26, 1974

[21] Appl. No.: 509,380

Related U.S. Application Data

[63] Continuation-in-part of Ser. No. 316,180, Dec. 18, 1970, abandoned.

[52] U.S. Cl.................................. 424/263; 424/251
[51] Int. Cl.² ................ A61K 31/44; A61K 31/505
[58] Field of Search............................ 424/251, 263

[56] References Cited
UNITED STATES PATENTS
2,731,382  1/1956  Basso et al......................... 424/251

Primary Examiner—Sam Rosen
Attorney, Agent, or Firm—Richard A. Thompson; Harry E. Westlake, Jr.

[57] ABSTRACT

Substituted 2- and 4-pyridones, pyrimidin-2- and 6-ones and tetrahydroquinolones when complexed with 4,4'-dinitrocarbanilide provide agents which are active coccidiostats and which produce minimal toxic side effects. Processes for the preparation of these complexes as well as compositions suitable for administration to poultry for the prevention and cure of coccidiosis are also disclosed.

7 Claims, No Drawings

ANTICOCCIDIAL COMPLEXES OF 4,4'-DINITROCARBANILIDES

This application is a continuation-in-part of U.S. Ser. No. 316,180, filed Dec. 18, 1972, now abandoned.

SUMMARY OF THE INVENTION

This invention relates generally to new and useful complexes of 4,4'-dinitrocarbanilide and processes for their preparation. In addition, this invention relates to the prevention and treatment of coccidiosis in poultry. More particularly it is concerned with the effectiveness of these 4,4'-dinitrocarbanilide complexes and with compositions containing said complexes. It is therefore an object of this invention to provide new complexes which possess antiparasitic and in particular coccidiostatic activity. Another object is to provide specifically for complexes which are active against the particular protozoa which causes coccidiosis in poultry. Still another object is to provide processes for the preparation of said complexes. Another object of this invention shall be the compositions containing said antiparasitic compounds for administration to poultry infected with coccidiosis or for the prevention of coccidiosis in poultry. Further objects will become apparent on a further reading of the description.

The complexes which have been found to be very active in treating and preventing coccidiosis in poultry are formed by complexing 4,4'-dinitrocarbanilide with a heterocyclic compound selected from among the following:

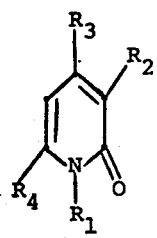

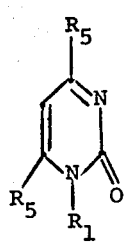

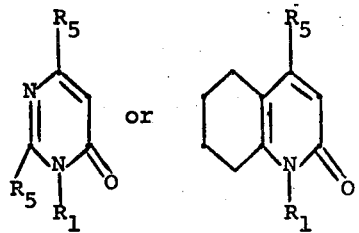

wherein $R_1$ is methyl or ethyl; $R_2$ is hydrogen or lower alkoxy; $R_3$ and $R_4$ are the same and are (a) lower alkyl when $R_2$ is hydrogen and (b) hydrogen when $R_2$ is lower alkoxy; and $R_5$ is lower alkyl.

Description of the Prior Art 4,4'-Dinitrocarbanilide has been complexed with other organic compounds and such complexes used for the prevention and treatment of coccidiosis. See for example U.S. Pat. Nos. 2,731,382; 2,731,383; and 2,731,384. However, the complexes of this invention are unexpectedly superior to the complexes of the prior art in several ways. The use level for the prior art complexes is the same as the maximum tolerated dose; that is, the therapeutic index is one. Thus the dose rate cannot be increased when a particularly difficult infection is encountered or when the particular strain of coccidiosis develops resistance to the drug being administered. Also manifestations of toxicity are encountered when the complex is used at its maximum tolerated dose. The most common effect is a weight depression which diminishes the health and the economic value of the poultry being treated.

The complexes of this invention are fully active at a level of administration which is far below the maximum tolerated dose, that is the therapeutic index is greater than one. As employed herein, the therapeutic index is defined as the ratio of the maximum tolerated dose to the minimum dose being administered which is still fully active. Thus a greater therapeutic index indicates a drug which is more highly tolerated. In the instant case the coccidiostatic compositions have a therapeutic index several times the prior art compounds. This results in a coccidiostat which is administered without the toxic manifestations of the prior art compounds, notably weight depression. In addition, the coccidiostats of this invention may be administered at doses higher than the minimum effective dosage in cases where such is warranted. This may be necessitated where the infection is particularly difficult and where resistant strains of coccidiosis develop. This is a major improvement which is totally surprising and which could not have been predicted by one skilled in this art.

Description of the Preferred Embodiments

The preferred embodiments of this invention are realized when, in the above structural formulae, $R_1$ is methyl or ethyl; $R_2$ is hydrogen or lower alkoxy; $R_3$ and $R_4$ are the same and are (a) lower alkyl when $R_2$ is hydrogen and (b) hydrogen when $R_2$ is lower alkoxy; and $R_5$ is lower alkyl.

The following heterocyclic compounds, when complexed with 4,4'-dinitrocarbanilide, are exemplary of the preferred embodiments of this invention but the list of compounds is not to be construed as exhaustive or limitative of the invention.

3-methoxy-1-methyl-2(1H)-pyridone 1,4,6-trimethyl-2(1H)-pyridone
1-methyl-4(1H)-pyridone
1,4-dimethyl-5,6,7,8-tetrahydro-2(1H)-quinolone
1,4,6-trimethyl-2(1H)-pyrimidinone
2,3,6-trimethyl-4(3H)-pyrimidinone
1-ethyl-4,6-dimethyl-2(1H)-pyrimidinone
1-ethyl-3-methoxy-2(1H)-pyridinone
1-ethyl-4,6-dimethyl-2(1H)-pyrimidinone Coccidiosis is a common and widespread poultry disease caused by several species of protozoan parasites of the genus Eimeria, such as *E. tenella*, *E. necatrix*, *E. acervulina*, *E. maxima*, *E. hagani*, and *E. brunetti*. *E. tenella* is the causative agent of a severe and often fatal infection of the caeca of chickens, which is manifested by severe and extensive hemorrhage, accumulation of blood in the caeca, and the passage of blood in the droppings. *E. necatrix* attacks the small intestine of the chick causing what is known as intestinal coccidiosis. Related species of coccidia such as *E. meleagridis* and *E. adenoides* are causative organisms of coccidiosis in turkeys. When left untreated, the severe forms of coccidiosis lead to poor weight gain, reduced feed efficiency and high mortality in fowl. The elimination or control of this disase is, therefore, of paramount importance to the poultry raising industry.

Therefore, another preferred embodiment of this invention are the compositions containing the above which may be successfully employed to cure and prevent the development of coccidiosis when administered to poultry. The active compounds are conveniently fed to poultry as a component of the feed of the animals although it may also be given suspended in the drinking water. According to a preferred aspect of the invention, novel compositions for the treatment of coccidiosis are provided which comprise one or more 4,4'-dinitrocarbanilide complexes intimately dispersed in or intimately admixed with an inert edible carrier or diluent. By an inert edible carrier or diluent is meant one that is nonreactive with respect to the complex and that may be administered with safety to the animals to be treated. The carrier or diluent is preferably one that is or may be an ingredient of the animal feed.

The compositions which are a preferred feature of this invention are the so-called feed supplements in which the 4,4'-dinitrocarbanilide complex is present in relatively large amounts and which are suitable for addition to the poultry feed either directly or after an intermediate dilution or blending step. Examples of carriers or diluents suitable for such compositions are animal feed ingredients such as distillers' dried grains, corn meal, citrus meal, fermentation residues, ground oyster shells, Attapulgus clay, wheat shorts, molasses solubles, corn cob meal, edible vegetable substances, toasted dehulled soya flour, soybean mill feed, antibiotic mycelia, soya grits, crushed limestone and the like. The complex is intimately dispersed or admixed throughout the solid inert carrier by methods such as grinding, stirring, milling, or tumbling. By selecting proper diluents and by altering the ratio of carrier to active ingredient, compositions of any desired concentration may be prepared. Formulations containing from about 1% to about 40% by weight and preferably from about 2–25% by weight, of the 4,4'-dinitrocarbanilide complex are particularly suitable for addition to poultry feedstuffs; those having from about 5–20% by weight of coccidiostat are very satisfactory. The active compound is usually dispersed or mixed uniformly in the diluent but in some instances may be sorbed on the carrier. Since it is convenient for the feed manufacturer to use about one pound of feed supplement for each ton of finished feed, the preferred concentration in the supplement is usually a function of the level of active ingredient desired in the finished feed.

Very low levels of 4,4'-dinitrocarbanilide complex in an animal feed are sufficient to afford the poultry good protection against coccidiosis. Preferably the compound is administered to chickens in an amount equal to about 0.00025% to 0.05% by weight of the medicated feed. Optimum results are obtained by feeding at a level of about 0.001 to 0.01% by weight of the medicated feed. For therapeutic treatment of an established coccidial infection, higher amounts of the complex, i.e. up to about 0.05% by weight of the feed consumed, may be employed. The most advantageous dosage level will, of course, vary somewhat with particular circumstances such as the type and severity of the coccidial infection to be treated.

For treating poultry, the feed supplement is uniformly dispersed in the animal feed by suitable mixing or blending procedures.

Usually the feed supplements are further diluted with materials such as corn meal or soybean meal before being incorporated in the animal feed. In this intermediate processing step the level of the 4,4'-dinitrocarbanilide complex in the carrier is brought down to about 0.01%–1.0% by weight. This dilution to facilitate uniform distribution of the coccidiostat in the finished feed. The finished feed is one that contains a source of fat, protein, carbohydrate, minerals, vitamins, and other nutritional factors.

In the above discussion of this invention, emphasis has been placed on solid compositions wherein the active ingredient is mixed with an edible carrier in a feed supplement, in a so-called premix or in the final poultry feedstuff. This is the preferred method of administering the complexes of this invention. An alternate method of treatment is to suspend the complex in the animals drinking water. The quantity of coccidiostat which may be administered in this fashion is, of course, limited by the quantity of the complex that may be suspended in the water without undue settling. Emulsifiers or surface active agents may be employed for this latter purpose.

This invention is not limited to coccidiostatic compositions having type 4,4'-dinitrocarbanilide complexes as the sole active ingredient. Also contemplated within its scope is what might be called "combined treatment" where a 4,4'-dinitrocarbanilide complex and one or more other coccidiostats are administered concurrently. For such purposes, compositions may be prepared containing this complex admixed with one or more other coccidiostats such as sulfaquinoxaline, other sulfa compounds, 4,4'-dinitrocarbanilide-2-hydroxy-4,6-dimethylpyrimidine complex, 3,3'-dinitrodiphenyldisulfide, 5-nitrofurfural semicarbazone, amprolium, zoalene, buquinolate, ethopabate, and the like.

It will likewise be understood by those skilled in this art that special feed supplement formulations and finished animal feeds containing vitamins, antibiotics, growth-promoting agents and other nutritional substances may include the complexes of this invention. A typical product of this type is the following:

| Ingredient: | Amount/lb. of Supplement, grams |
| --- | --- |
| Riboflavin | 0.64 |
| DL-calcium panththenate. | 2.10 |
| Niacin | 3.67 |
| Choline chloride | 50.00 |
| Vitamin $B_{12}$ concentrate. | 1.30 mg. |
| Procaine penicillin | 0.84 |
| Vitamin A (100,000 u./g.) | 3.38 |
| Vitamin $D_3$ (200,000 u./g.) | 0.68 |
| Arsanilic acid | 18.36 |
| Butylated hydroxy toluene | 23.15 |
| DL-methionine | 23.15 |
| 4,4'-Dinitrocarbanilide/3-methoxy-1-methyl-2-pyridone complex | 23.00 |
| Distiller's grains to 1 pound. | |

Animal feed supplements having the following compositions are prepared by intimately mixing the 4,4'-dinitrocarbanilide complex and the particular edible solid diluent or diluents:

| | | lbs. |
| --- | --- | --- |
| A. | 4,4'-Dinitrocarbanilide/3-methoxy-1-methyl-2-pyridone complex | 7.5 |
| | Distiller's dried grains | 92.5 |
| B. | 4,4'-Dinitrocarbanilide/1,4,6-trimethyl-pyrimidine-2-one complex | 5.0 |
| | Soybean mill feed | 50.0 |
| | Fine soya grits | 45.0 |
| C. | 4,4'-Dinitrocarbanilide/1,4-dimethyl-5,6,7,8-tetrohydroquinoline complex | 10.0 |
| | Molasses solubles | 90.0 |
| D. | 4,4'-Dinitrocarbanilide/3-methoxy-1-methyl-2-pyridone complex | 15.0 |
| | Corn distiller's grains | 55.0 |
| | Corn germ meal | 30.0 |
| E. | 4,4'-Dinitrocarbanilide/1,4,6-trimethyl-pyrimidine-2-one complex | 20.0 |
| | Wheat shorts | 30.0 |
| | Distiller's dried grains | 50.0 |
| F. | 4,4'-Dinitrocarbanilide/1,4-dimethyl-5,6,7,8-tetrahydroquinoline complex | 25.0 |
| | Corn distiller's dried grains | 75.0 |

These supplements are made by mechanical milling or mixing of the ingredients to insure uniform distribution of the active compound.

The antiparasitic 4,4'-dinitrocarbanilide complexes are prepared by contacting one of the heterocyclic compounds above with 4,4'-dinitrocarbanilide. It is preferred that the heterocyclic compound be dissolved in a solvent and the resulting solution combined with undissolved 4,4'-dinitrocarbanilide. It is not necessary that the reactants be very soluble in the solvent employed. The progress of the reaction can be followed by observing the precipitation of the insoluble complex. When one of the compounds is sparingly soluble in the solvent employed, the reaction can be followed by observing the exchange of the undissolved heterocyclic compound with the precipitated complex. When no further complex is precipitated, the reaction is complete. The initial production of a thick precipitate of the complex is generally very fast, taking from 1 to 15 minutes; however, to insure optimum yields the reaction is generally stirred for an additional period of 1 to 24 hours. The reaction is generally run at ambient temperatures, however, temperatures of from 0° to 25°C. may be employed where the reaction is exothermic; and temperatures of from 25° to 75°C. may be employed where the complex is slow to form. The heterocyclic compound is generally reacted in excess of the 4,4'-dinitrocarbanilide said excess being from 10 to 200%. The unreacted excess heterocyclic compound is generally recoverable from the reaction mixture and may reused.

The nature of the solvents aforementioned is not critical to the success of the reaction. Polar and nonpolar solvents may be employed along with protic or aprotic solvents. Mixtures of solvents has often proven successful. The solvent may be an ether such as dioxane ethyl ether, 2,2'-diethoxyethyl ether and the like; an alcohol such as the lower (1 to 6 carbon atoms) aliphatic alcohols; loweraliphatic hydrocarbons; aromatic hydrocarbons, such as benzene, toluene, or xylene; water and the like. It has been found to be advantageous to employ a solvent or solvent mixture which the heterocyclic compound is soluble and the 4,4'-dinitrocarbanilide is sparingly soluble.

The heterocyclic compounds employed in the preparation of the novel complexes of this invention are generally known in the art. However, following the examples of this invention is a compilation of Preparations describing the synthesis of those heterocycles which have not previously been prepared. Where a particular heterocyclic compound is known in this art, a literature reference to the preparation thereof has been supplied. The heterocyclic compounds of this invention are generally prepared by reacting a methyl or ethyl halide, preferably iodide, with the 1-unsubstituted analagous compound. The reaction preferably is run in the presence of an inorganic base such as an alkali metal hydroxide.

The preparation of 1-ethyl-4,6-dimethyl-2(1H)-pyrimidone is somewhat different, being prepared by the reaction of acetyl acetone and ethyl urea in the presence of an acid. The preparation of other heterocyclic compounds will be apparent to one skilled in this art.

The following examples are presented in order that this invention might be more fully understood. It is not intended for these examples to be limitative of this invention and they should not be so construed. Note: The yields in the following examples are calculated on the basis of the amount of 4,4'-dinitrocarbanilide employed.

EXAMPLE 1

4,4'-Dinitrocarbanilide.1-Methyl-3-Methoxy-2(1H)-Pyridone complex 41.7 G. (0.03 moles) of 1-methyl-3-methoxy-2(1H)-pyridone is dissolved in 225 ml. of methanol and 100 ml. of toluene. 72.0 G. (0.24 moles) of 4,4'-dinitrocarbanilide is added and a thick beige solid is immediately formed. The slurry is stirred overnight at room temperature, collected by filtration, washed with hexane, and dried in air. There is obtained 103.9 g. (100%) of 4,4'-dinitrocarbanilide.1-methyl-3-methoxy-2(1H)-pyridone complex.

EXAMPLE 2

4,4'-Dinitrocarbanilide.1,4,6-Trimethyl-2(1H)-Pyridone Complex 20.5 G. (0.15 moles) of 1,4,6-trimethyl-2(1H)-pyridone is dissolved in 75 ml. of methanol. 30.2 g. (0.10 moles) of 4,4'-dinitrocarbanilide is added and the thick brown slurry resulted. An additional quantity of methanol (25 ml.) is added and the reaction mixture stirred overnight at room temperature. The solid material is collected by filtration, washed with hexane, and dried in air affording 42.6 g. (99%) of 4,4'-dinitrocarbanilide.1,4,6-trimethyl-2(1H)-pyridone complex.

EXAMPLE 3

4,4'-Dinitrocarbanilide.1-Methyl-4(1H)-Pyridone Complex 2.18 G. (0.02 moles) of 1-methyl-4(1H)-pyridone is dissolved in 15 ml. of methanol. 3.02 g. (0.01 moles) of 4,4'-dinitrocarbanilide is added and immediately a thick beige precipitate is formed. The slurry is stirred overnight at room temperature, collected by filtration and dried in air affording 4.2 g. (100%) of 4,4'-dinitrocarbanilide.1-methyl-4(1H)-pyridone complex.

EXAMPLE 4

4,4'-Dinitrocarbanilide.1,4,6-Trimethyl-2(1H)-Pyrimidinone Complex 20.7 G. (0.15 moles) of 1,4,6-trimethyl-2(1H)-pyrimidinone is dissolved in 75 ml. of methanol and combined with 32.0 g. (0.11 moles) of 4,4'-dinitrocarbanilide. The resulting thick slurry is diluted with 25 ml. of methanol and stirred at room temperature overnight. The solid material is filtered, washed with ether, and dried in air affording 42.5 g. (97%) of 4,4'-dinitrocarbanilide.1,4,6-trimethyl-2(1H)-pyrimidinone complex.

EXAMPLE 5

4,4'-Dinitrocarbanilide.2,3,6-Trimethyl-4(3H)-Pyrimidinone Complex 1.38 G. (0.01 moles) of 2,3,6-trimethyl-4(3H)-pyrimidinone is dissolved in a minimum amount of methanol and combined with 1.50 g. (0.005 moles) of 4,4'-dinitrocarbanilide. The thick slurry is stirred at room temperature for 2 days. The reaction mixture is filtered and the solid material washed with a small amount of ether/hexane (1:1) and dried in air. There is afforded 2.10 g. (100%) of 4,4'-dinitrocarbanilide.2,3,6-trimethyl-4(3H)-pyrimidinone complex.

EXAMPLE 6

4,4'-Dinitrocarbanilide.1-Ethyl-4,6-Dimethyl-2(1H)-Pyridone Complex 1.20 G. (0.0075 moles) of 1-ethyl-4,6-dimethyl-2(1H)-pyridone is dissolved in 20 ml. of dimethoxyethane. 1.51 G. (0.005 moles) of 4,4'-dinitrocarbanilide is added and a beige precipitate is formed which is stirred overnight at room temperature. The solid material is collected by filtration, washed with hexane, and dried in air affording 1.50 g. (65%) of 4,4'-dinitrocarbanilide.1-ethyl-4,6-dimethyl-2(1H)-pyridone complex.

EXAMPLE 7

4,4-Dinitrocarbanilide.1-Ethyl-3-Methoxy-2(1H)-Pyridone Complex 13.8 G. (0.09 moles) of 1-ethyl-3-methoxy-2(1H)-pyridone is dissolved in 75 ml. of methanol. 18.5 G. (0.06 moles) of 4,4'-dinitrocarbanilide is added and the resulting slurry is stirred overnight at room temperature. The solid precipitate is collected by filtration and dried in air affording 25.4 g. (93%) of 4,4'-dinitrocarbanilide.1-ethyl-3-methoxy-2(1H)-pyridone complex.

EXAMPLE 8

4,4'-Dinitrocarbanilide.1-Ethyl-4,6-Dimethyl-2(1H)-Pyrimidinone Complex 3.04 G. (0.02 moles) of 1-ethyl-4,6-dimethyl-2(1H)-pyrimidinone is dissolved in 12 ml. of methanol and combined with 3.02 g. (0.01 moles) of 4,4'-dinitrocarbanilide. The resultant slurry is stirred overnight at room temperature. The solid material is collected by filtration and dried in air affording 4.3 g. (95%) of 4,4'-dinitrocarbanilide.1-ethyl-4,6-dimethyl-2(1H)-pyrimidinone complex.

EXAMPLE 9

4,4'-Dinitrocarbanilide.1,4-Dimethyl-5,6,7,8-Tetrahydro-2(1H)-Quinolone Complex 1.77 G. (0.01 moles) of 1,4-dimethyl-5,6,7,8-tetrahydro-2(1H)-quinolone is dissolved in a minimum amount of ether. 1.50 G. (0.005 moles) of 4,4'-dinitrocarbanilide is added and the resultant slurry is stirred at room temperature for two days. The precipitate is collected by filtration, washed with hexane, and dried affording 2.15 g. (90%) of 4,4'-dinitrocarbanilide.1,4-dimethyl-5,6,7,8-tetrahydro-2(1H)-quinolone complex.

The heterocyclic complexing agents may be prepared by the following procedures. Where the compound is new a full preparation is described, and where the compound is known in the art, the listed literature references will describe the preparation.

PREPARATION 1

1-Methyl-3-Methoxy-2(1H)-Pyridone

A mixture of 3-methoxy-2(1H)-pyridone (25 g., 0.2 moles), potassium hydroxide (16 g., 0.24 moles) and methyl iodide (45.4 g., 0.32 moles) in 400 ml. methanol is heated at reflux for 5 hours. The methanol is removed under reduced pressure leaving a solid residue which is extracted with methylene chloride. The methylene chloride extracts are washed with water, a saturated salt solution, and dried over sodium sulfate. Evaporation of the dried extracts, under reduced pressure, affords 1-methyl-3-methoxy-2(1H)-pyridone as a colorless oil which solidifies on standing (26.2 g., 94%). The pyridone is very hygroscopic and rapidly liquifies on exposure to air.

PREPARATION 2

1,4,6-Trimethyl-2(1H)-Pyridone

Lit. Ref.: J. Elvidge and L. Jackman, J. Chem. Soc., 859 (1961).

PREPARATION 3

1-Methyl-4(1H)-Pyridone

Lit. Ref.: R. Toomey and E. Riegel, J. Org. Chem., 17, 1492 (1952).

PREPARATION 4

1,4,6-Trimethyl-2(1H)-Pyrimidinone

Lit. Ref.: W. J. Hale, J. Am. Chem. Soc., 36, 104 (1914).

PREPARATION 5

2,3,6-Trimethyl-4(3H)-Pyrimidinone

Lit. Ref.: R. Gompper, Chem. Ber., 93, 198 (1960).

PREPARATION 6

1-Ethyl-4,6-Dimethyl-2(1H)-Pyridone

A mixture of 4,6-dimethyl2(1H)-pyridone (2.46 g., 0.02 moles), potassium hydroxide (1.58 g., 0.024 moles) and ethyl iodide (6.24 g., 0.04 moles) in 50 ml. ethanol is heated at reflux for 3 hours. The ethanol is removed under vacuum leaving a solid residue which is extracted with methylene chloride. The methylene chloride extracts are washed with 2.5 N sodium hydroxide, water, a saturated salt solution, and dried over sodium sulfate. Evaporation of the dried extracts affords 1-ethyl-4,6-dimethyl-2(1H)-pyridone as a pale yellow oil (1.5 g., 48%) which shows a single spot on thin layer chromatography.

PREPARATION 7

1-Ethyl-3-Methoxy-2(1H)-Pyridone

A mixture of 3-methoxy-2(1H)-pyridone (12.5 g., 0.10 moles), potassium hydroxide (8.0 g., 0.12 moles) and ethyl iodide (31.2 g., 0.02 moles) in 200 ml. ethanol is heated at reflux for 4 hours. Proceeding as previous preparations affords 1-ethyl-3-methoxy-2(1H)-pyridone as a clear yellow oil (14.1 g., 92%).

PREPARATION 8

1-Ethyl-4,6-Dimethyl-2(1H)-Pyrimidinone

Acetylacetone (9.0 g., 0.09 moles) and ethylurea (7.13 g., 0.081 moles) are dissolved in 30 ml. ethanol. The solution is cooled in an ice-water bath while 30 g. of cold concentrated sulfuric acid is added. The resulting yellow solution is stored at room temperature for 10 days and diluted with a large volume of ether. The ether-ethanol mixture is decanted from the thick syrupy residue which is washed with additional fresh ether. The residue is made basic with 2.5 N sodium hydroxide and extracted throughly with methylene chloride. The organic extracts are dried over sodium sulfate, treated with charcoal, filtered, and evaporated under vacuum affording 1-ethyl-4,6-dimethyl-2(1H)-pyrimidinone as a tan solid (7.6 g., 62%).

PREPARATION 9

A. 2-Hydroxy-4-Methyl-5,6,7,8-Tetrahydroquinoline 98.15 G. (1.0 mole) of cyclohexanone, 130 g. (1.0 mole) of ethylacetoacetate and 77.1 g. (1.0 mole) of ammonium acetate are heated at reflux for 14 hours. The reaction mixture is cooled in ice and diluted with water. The resultant precipitate is collected by filtration, washed with ether and dried in air affording 8.0 g (5%) of 2-hydroxy-4-methyl-5,6,7,8-tetrahydroquinoline, m.p. 250°-252°C.

B. 1,4-Dimethyl-5,6,7,8-Tetrahydro-2(1H)-Quinolone 7.20 G. (0.044 moles) of 2-hydroxy-4-methyl-5,6,7,8-tetrahydroquinoline, 2.96 g. (0.0528 moles) of potassium hydroxide and 9.9 g. (0.07 moles) of methyl iodide in 50 ml. of methanol are combined and heated at reflux for 5 hours. The methanol is removed in vacuo and the residue extracted with methylene chloride. The methylene chloride extracts are washed with water, saturated salt solution and dried over sodium sulfate. Evaporation of the dried extracts under reduced pressure affords 6.25 g. (80%) of 1,4-dimethyl5,6,7,8-tetrahydro-2(1H)-quinolone.

What is claimed is:

1. A composition for the prevention and cure of coccidiosis which comprises an inert carrier and an effective amount of one or more complexes of 4,4'-dinitrocarbanilide and one of the heterocyclic compounds having the formula:

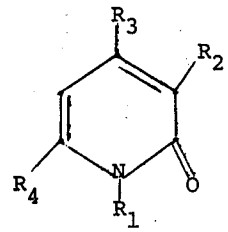

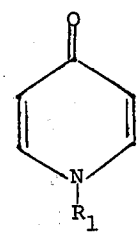

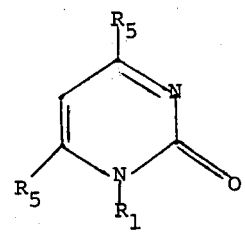

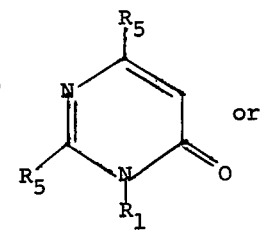 or 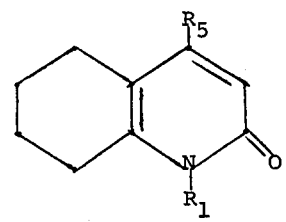

wherein $R_1$ is methyl or ethyl; $R_2$ is hydrogen or lower alkoxy; $R_3$ and $R_4$ are the same and are (a) lower alkyl when $R_2$ is hydrogen and (b) hydrogen when $R_2$ is lower alkoxy; and $R_5$ is lower alkyl.

2. The composition of claim 1 which is a medicated feed composition suitable for administration to poultry.

3. The composition of claim 2 in which the active complex is present in from 0.00025 to 0.05% by weight of the finished feed composition.

4. The composition of claim 3 in which the active complex is present in from 0.001 to 0.01% by weight of the finished feed composition.

5. The composition of claim 1 in which the heterocyclic compound is 3-methoxy-1-methyl-2(1H)-pyridone.

6. The composition of claim 1 in which the active complex is present in from 5 to 20% by weight.

7. A feed supplement which comprises an inert carrier and one or more complexes of 4,4'-dinitrocarbanilide and one of the heterocyclic compounds having the formula:

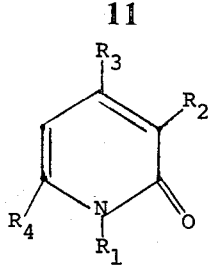
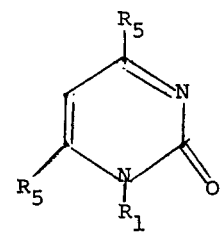
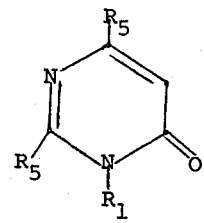
or
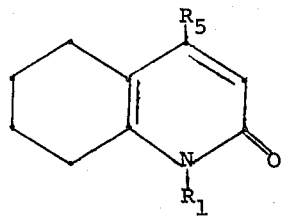
wherein $R_1$ is methyl or ethyl; $R_2$ is hydrogen or lower alkoxy; $R_3$ and $R_4$ are the same and are (a) lower alkyl when $R_2$ is a hydrogen and (b) hydrogen when $R_2$ is lower alkoxy; and $R_5$ is lower alkyl and wherein said one or more complexes is from about 2–25% by weight of said feed supplement.
* * * * *